United States Patent [19]

Doherty et al.

[11] Patent Number: 4,547,371
[45] Date of Patent: Oct. 15, 1985

[54] SUBSTITUTED CEPHALOSPORIN SULFONES AS ANTI-INFLAMMATORY AND ANTI-DEGENERATIVE AGENTS

[75] Inventors: James B. Doherty, New Milford; Bonnie M. Ashe, Scotch Plains; Paul E. Finke, Metuchen; Shrenik K. Shah, Clark; Kevan R. Thompson, Westfield; Morris Zimmerman, Watchung, all of N.J.

[73] Assignee: Merck & Co., Inc., Rahway, N.J.

[21] Appl. No.: 485,978

[22] Filed: Apr. 18, 1983

[51] Int. Cl.$^4$ ............... C07D 501/20; A61K 31/545
[52] U.S. Cl. .................................... 514/200; 544/16; 544/30; 544/26; 544/27
[58] Field of Search ............... 424/246; 544/30, 16, 544/26, 27

[56] References Cited

U.S. PATENT DOCUMENTS

| | | | |
|---|---|---|---|
| 4,271,157 | 6/1981 | Denzel et al. | 544/28 |
| 4,283,397 | 8/1981 | Hannah | 544/28 |
| 4,294,827 | 10/1981 | Preiss et al. | 544/28 |
| 4,459,405 | 7/1984 | Hall | 544/28 |

FOREIGN PATENT DOCUMENTS 53-3015395  2/1978  Japan.
1603212  11/1981  United Kingdom.

OTHER PUBLICATIONS

J. R. Corfield et al., Tetrahedron Letters, No. 32, 2915 (1978).
J. C. Jaszebernyi et al., Acta Chimica Academiae Scientiarum Hungaricae tomers 98(1) p. 105 (1978).
T. E. Gunda et al., Acta, Chemica Scandinavica B, p. 33, (1983).

*Primary Examiner*—Nicholas S. Rizzo
*Attorney, Agent, or Firm*—Theresa Y. Cheng; Mario A. Monaco

[57] ABSTRACT

Substituted cephalosporin sulfones are found to be potent elastase inhibitors and thereby useful anti-inflammatory/antidegenerative agents.

7 Claims, No Drawings

SUBSTITUTED CEPHALOSPORIN SULFONES AS ANTI-INFLAMMATORY AND ANTI-DEGENERATIVE AGENTS

BACKGROUND OF THE INVENTION

We have found that sulfones of substituted cephalosporins are potent elastase inhibitors and therefore are useful anti-inflammatory/antidegenerative agents.

Proteases from granulocytes and macrophages have been reported to be responsible for the chronic tissue destruction mechanisms associated with inflammation, including rheumatoid arthritis and emphysema. Accordingly, specific and selective inhibitors of these proteases are candidates for potent anti-inflammatory agents useful in the treatment of inflammatory conditions resulting in connective tissue destruction, e.g. rheumatoid arthritis, emphysema, bronchial inflammation, osteoarthritis, spondylitis, lupus, psoriasis and acute respiratory distress syndrome.

The role of proteases from granulocytes, leukocytes or macrophages are related to a rapid series of events which occurs during the progression of an inflammatory condition:

(1) There is a rapid production of prostaglandins (PG) and related compounds synthesized from arachidonic acid. This PG synthesis has been shown to be inhibited by aspirin-related nonsteroidal anti-inflammatory agents including indomethacin and phenylbutazone. There is some evidence that protease inhibitors prevent PG production;

(2) There is also a change in vascular permeability which causes a leakage of fluid into the inflamed site and the resulting edema is generally used as a marker for measuring the degree of inflammation. This process has been found to be induced by the proteolytic or peptide cleaving activity of proteases, especially those contained in the granulocyte, and thereby can be inhibited by various synthetic protease inhibitors, for example, N-acyl benzisothiazolones and the respective 1,1-dioxides. Morris Zimmerman et al., *J. Biol. Chem.*, 255, 9848 (1980); and B. Ashe et al., *J. Biol. Chem.*, 256, 11603 (1981).

(3) There is an appearance and/or presence of lymphoid cells, especially macrophages and polymorphonuclear leukocytes (PMN). It has been known that a variety of proteases are released from the macrophages and PMN, further indicating that the proteases do play an important role in inflammation.

In general, proteases are an important family of enzymes within the peptide bond cleaving enzymes whose members are essential to a variety of normal biological activities, such as digestion, formation and dissolution of blood clots, the formation of active forms of hormones, the immune reaction to foreign cells and organisms, etc., and in pathological conditions such as the degradation of structural proteins at the articular cartilage/pannus junction in rheumatoid arthritis etc.

Elastase is one of the proteases. It is an enzyme capable of hydrolyzing the connective tissue component elastin, a property not contained by the bulk of the proteases present in mammals. It acts on a protein's nonterminal bonds which are adjacent to an aliphatic amino acid. Neutrophil elastase is of particular interest because it has the broadest spectrum of activity against natural connective tissue substrates. In particular, the elastase of the granulocyte is important because, as described above, granulocytes participate in acute inflammation and in acute exacerbation of chronic forms of inflammation which characterize many clinically important inflammatory diseases.

Proteases may be inactivated by inhibitors which block the active site of the enzyme by binding tightly thereto. Naturally occurring protease inhibitors form part of the control or defense mechanisms that are crucial to the well-being of an organism. Without these control mechanisms, the proteases would destroy any protein within reach. The naturally occurring enzyme inhibitors have been shown to have appropriate configurations which allow them it to bind tightly to the enzyme. This configuration is part of the reason that inhibitors bind to the enzyme so tightly (see Stroud, "A Family of Protein-Cutting Proteins" *Sci. Am.* July 1974, pp. 74–88). For example, one of the natural inhibitors, $\alpha_1$-Antitrypsin, is a glycoprotein contained in human serum that has a wide inhibitory spectrum covering, among other enzymes, elastase both from the pancreas and the PMN. This inhibitor is hydrolyzed by the proteases to form a stable acyl enzyme in which the active site is no longer available. Marked reduction in serum $\alpha_1$-antitrypsin, either genetic or due to oxidants, has been associated with pulmonary emphysema which is a disease characterized by a progressive loss of lung elasticity and resulting respiratory difficulty. It has been reported that this loss of lung elasticity is caused by the progressive, uncontrolled proteolysis or destruction of the structure of lung tissue by proteases such as elastase released from leukocytes. J. C. Powers, *TIBS*, 211 (1976).

Rheumatoid arthritis is characterized by a progressive destruction of articular cartilage both on the free surface bordering the joint space and at the erosion front built up by synovial tissue toward the cartilage. This destruction process, in turn, is attributed to the protein-cutting enzyme elastase which is a neutral protease present in human granulocytes. This conclusion has been supported by the following observations:

(1) Recent histochemical investigations showed the accumulation of granulocytes at the cartilage/pannus junction in rheumatoid arthritis; and (2) a recent investigation of mechanical behavior of cartilage in response to attack by purified elastase demonstrated the direct participation of granulocyte enzymes, especially elastase, in rheumatoid cartilage destruction. H. Menninger et al., in *Biological Functions of Proteinases*, H. Holzer and H. Tschesche, eds. Springer-Verlag, Berlin, Heidelburg, New York, 1979, pp. 196–206.

Accordingly, an object of this invention is to discover new protease inhibitors, especially elastase inhibitors, useful for controlling tissue damage and various inflammatory or degenerative conditions mediated by proteases particularly elastase.

Another object of the present invention is to provide pharmaceutical compositions for administering the active substituted cephalosporin sulfones as protease inhibitors.

Still a further object of this invention is to provide a method of controlling inflammatory conditions by administering a sufficient amount of one or more of the active, substituted cephalosporin sulfones in a mammalian species in need of such treatment.

DETAILED DESCRIPTION OF THE INVENTION

This invention relates to cephalosporin sulfones as potent elastase inhibitors useful in the prevention, control and treatment of inflammatory conditions especially arthritis and emphysema.

Some of the cephalosporin free acids are known antibiotics which have been described in U.S. Pat. No. 4,297,488 issued Oct. 27, 1981.

The structural formula of the cephalosporin sulfones of the present invention are represented as follows:

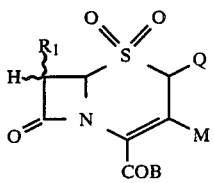

wherein M is:
(1) trifluoromethyl;
(2) chloro or fluoro;
(3) —COOH;
(4) —CHO; or
(5) —CH$_2$A wherein A represents
(a) hydrogen;
(b) halo;
(c) hydroxy;
(d) alkoxy;
(e) aryloxy;
(f) aralkyloxy;
(g) unsubstituted or substituted mercapto;
(h) acylthio;
(i) acyloxy especially C$_{2-6}$ alkanoyloxy or arylcarbonyloxy such as acetoxy, benzyloxycarbonyloxy, benzoyloxy, succinoyloxy, substituted or unsubstituted carbamoyl, thiocarbamoyl and N-alkyl or N,N-dialkyl derivatives thereof;
(j) a quaternary ammonium group, for example,

where E represents loweralkyl, aryl or aralkyl;
(k) a substituted or unsubstituted amino or amido group especially NH$_2$ or —CONH$_2$ and N-alkyl or N,N-dialkyl derivatives thereof.

Thus, CH$_2$A can be a halomethyl such as chloromethyl, bromomethyl or fluoromethyl.

When CH$_2$A is a substituted hydroxy or substituted mercapto group, it can be shown by the formula

where Z is oxygen or sulfur, and R$_5$ is an acyl group; a straight chain or branched chain loweralkyl, alkenyl or alkynyl group; an aryl group; an aralkyl group; or a heterocyclic group such as heteroaryl, heterocycloalkyl e.g., 1,3-dioxacyclohex-4-yl, piperidino, morpholino, oxacyclopropyl, pyrrolidino, tetrazolo, benzothiazolo, imidazolidino, pyrazolidino, and piperazino; or heterocycloalkenyl such as pyrrolino, 2-imidazolino, 3-pyrazolino or isoindolino. These groups can be unsubstituted or can be substituted by radicals such as alkyl, alkoxy, halo, cyano, carboxy, carbamoyl, azido,, sulfo, amino,, substituted amino, haloalkyl, carboxyalkyl, carbamoylalkyl, N-substituted carbamoylalkyl, guanidino, N-substituted guanidino, guanidoalkyl, sulfamyl, substituted sulfamyl, and the like. Representative of the CH$_2$A groups are methoxymethyl, n-propoxymethyl, methylthiomethyl, acetoxymethyl, propionyloxymethyl, benzoyloxymethyl, (p-chlorobenzoyl)oxymethyl, succinoyloxymethyl, (p-methylbenzoyl)oxymethyl, pivaloyloxymethyl, (1-adamantyl)-carboxymethyl, butanoyloxymethyl, carbamoyloxymethyl, (N-methylcarbamoyl)oxymethyl, (N-ethylcarbamoyl)oxymethyl, [N-(2-chloroethyl)carbamoyl]oxymethyl, (N-phenylcarbamoyl)oxymethyl, [N-(carboxymethyl)carbamoyl]oxymethyl, (N-p-sulfophenyl-carbamoyl)oxymethyl, p-carboxymethylphenyl-carbamoyloxymethyl, methoxycarbonyloxymethyl, isobutanoyloxymethyl, cyclobutylcarbonyloxymethyl, carbamoylthiomethyl, (ethoxythiocarbonyl)thiomethyl, (n-propoxythiocarbonyl)thiomethyl, (cyclopentanoxythiocarbonyl)thiomethyl, methylthiomethyl, N,N-diethylthiocarbamoylthiomethyl, N-methylpiperazinium-1-thiocarbonylthiomethyl, N,N-dimethylpiperazinium-1-thiocarbonylthiomethyl, 2-furoylthiomethyl, isothiouroniummethyl, (5-methyl-1,3,4-thiadiazol-2-yl)thiomethyl, p-tolylsulfonylthiomethyl, 2-benzothiazolothiomethyl, mesyloxymethyl, 1-methyl-1,2,3,4-tetrazolyl-5-thiomethyl, tosyloxymethyl, sulfamoyloxymethyl, 1-naphthoyloxymethyl, 2-furylacetoxymethyl, cinnamoyloxymethyl, p-hydroxycinnamoyloxymethyl, p-sulfocinnamoyloxymethyl and 1R:2S-epoxypropylphosphonyloxymethyl.

Alternatively, when CH$_2$A is hydroxymethyl, the cephalosporin can also exist as the lactone which is formed by internal esterification with the adjacent carboxy group.

The substituent CH$_2$A can also be a group of the general formula

wherein Y$_1$ represents amino or substituted amino including nitrogen heterocycles and substituted heterocyclic groups as described for R$_5$. Y$_1$ may also be nitrogen which is part of the heterocyclic system as shown below.

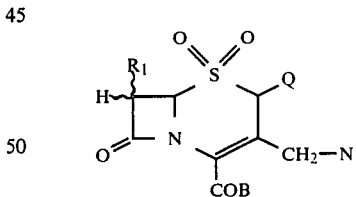

Examples of such groups that might be mentioned are aminomethyl, acetamidomethyl, carbamoylaminomethyl, N,N-dimethylaminomethyl, N-(2-chloroethyl)aminomethyl, 5-cyano-triazol-1-yl-methyl, 4-methoxycarbonyltriazol-1-yl-methyl.

When A is amino the cephalosporin compound can also exist as the lactam formed by loss of water with the adjacent carboxy group.

Representative of the quaternary ammonium groups representing A that might be mentioned are pyridinium, 3-methylpyridinium, 4-methylpyridinium, 3-chloropyridinium, 3-bromopyridinium, 3-iodopyrinium, 4-carbamoylpyridinium, 4-(N-hydroxymethylcarbamoyl)pyridinium, 4-(N-carbomethoxycarbamoyl)pyridinium, 4-(N-cyanocarbamoyl)pyridinium, 4-carboxymethylpyridinium, 4-hydroxymethylpyridinium, 4-trifluoromethyl-pyridinium, quinolinium, picolinium and lutidinium.

When A is mercapto, it may be —SH,

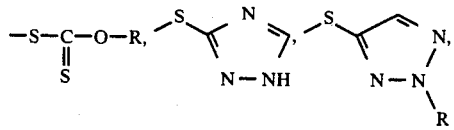
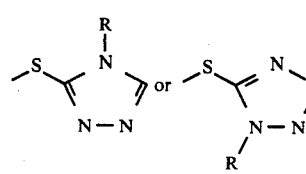

alkyl, alkylthio, arylthio, aralkylthio or heterocyclothio, wherein R represents $C_{1-6}$loweralkyl.

The preferred groups representing A are (a) hydrogen; (b) halo; (c) hydroxy; (d) alkoxy; (e) aryloxy; (f) aralkyloxy; (g) substituted or unsubstituted mercapto especially

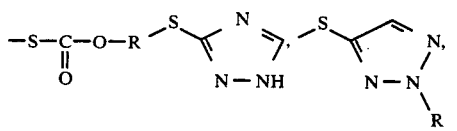
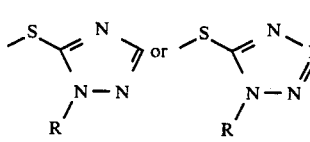

(h) acylthio; or (i) acyloxy. The acyl group can be a loweralkanoyl group of 2–6 carbon atoms such as acetyl, —$COC_2H_5$ or —$COC_3H_7$, carbamoyl, or thiocarbamoyl and N-alkyl or N,N-dialkyl derivatives thereof. The alkyl group of the foregoing substituents contains 1–10 carbon atoms and may be further substituted by radicals such as alkoxy, halo, amino, cyano, carboxy, sulfo, and the like.

More preferably, A is
(a) alkanoyloxy especially

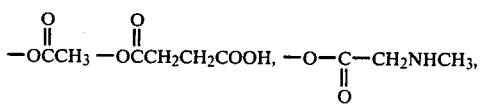
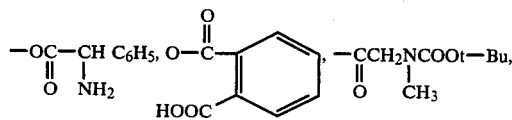
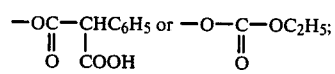

(b) $C_{1-3}$ alkoxy especially methoxy, ethoxy or i- or n-propyloxy;
(c) halo;
(d) hydrogen;
(e) hydroxy;
(f) substituted or unsubstituted mercapto; or (g) carbamoyloxy, especially L- or D-form of

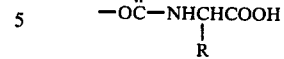

The substituent $R_1$ in formula (I) above can be R'NH—, where R' represents a substituted or unsubstituted aliphatic, aromatic or heterocyclic, araliphatic or heterocyclylaliphatic carboxylic acid radical or a carbothioic acid radical such as the acyl radicals of the known cephalosporins and penicillins. These acyl radicals can be represented by the general formula $$-CO(CH)_m(CH_2)_nR_3$$
$$\phantom{-CO(CH)_m}|$$
$$\phantom{-CO(CH)_m}R_2$$

where $R_2$ is a radical of the group defined below, m and n independently represent 0–4 and $R_3$ represents R" or ZR", which are also defined below.

One group of the acyl radicals, i.e., when m and n are both 0 and $R_3$ is R", can be represented by the general formula

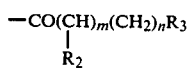

wherein R" is:

(a) straight or branched chain alkyl having from 1 to 20 carbon atoms especially methyl, trifluoromethyl, ethyl, isopropyl, t-butyl, pentyl or hexyl;

(b) aryl having from 6 to 10 carbon atoms especially phenyl, substituted phenyl or naphthalene;

(c) cycloalkyl having from 3 to 8 carbon atoms especially cyclopentyl, or cyclohexyl;

(d) alkenyl having from 2 to 20 carbon atoms especially $C_{2-6}$alkenyl such as vinyl, allyl, or butenyl;

(e) cycloalkenyl having from 5 to 8 carbon atoms especialy cyclopentenyl or cyclohexenyl;

(f) alkynyl having from 2 to 20 carbon atoms especially $C_{2-6}$alkynyl for example, ethynyl, propynyl or hexynyl;

(g) alkoxy having from 1 to 10 carbon atoms especially $C_{1-3}$ alkoxy such as methoxy, ethoxy or n-propoxy or i-propoxy;

(h) aralkyl, alkaryl, aralkenyl, aralkynyl, alkenylaryl or alkynylaryl wherein alkyl, aryl, alkenyl and alkynyl are as previously defined;

(i) monoheteroaryl, di- or polyheteroaryl, or fused heteroaryl containing from 1 to 3 of any one or more of the heteroatoms N, S or O in each heteroaryl ring thereof, for example, pyridyl, pyrryl, thienyl, isothiazolyl, imidazolyl, pyrazinyl, pyrimidyl quinolyl, isoquinolyl, benzothienyl, isobenzofuryl, pyrazolyl, indolyl, purinyl, carbozolyl, isoxazolyl and the like;

(j) heteroarylalkyl such as 2-pyridylmethyl, 2-thienylmethyl and 3-isothiazolylethyl; or (k) hydrogen.

The above groups (a)–(j) can be unsubstituted or can be substituted by radicals such as alkyl, alkoxy, halo such as fluoro, chloro, bromo or iodo, cyano, carboxy, sulfoamino, carbamoyl, sulfonyl, azido, amino, substituted amino such as monoalkylamino and dialkylamino, haloalkyl, carboxyalkyl, carbamoylalkyl, N-substituted carbamoylalkyl, guanidino, N-substituted guanidino, guanidinoalkyl, and the like. Representative examples of such acyl groups that might be mentioned are those wherein R" is methoxy, ethoxy, benzyl, p-hydroxybenzyl, 3- or 4-nitrobenzyl, p-aminobenzyl, o-aminobenzyl, m-aminobenzyl, o-sulfobenzyl, p-carboxymethylbenzyl, p-carbamoylmethylbenzyl, m-fluorobenzyl, m-bromobenzyl, p-chlorobenzyl, p-methoxybenzyl, p-aminomethylbenzyl, hydrogen, methyl, ethyl, cyanomethyl, 2-pentenyl, n-amyl, n-heptyl, phenethyl, difluoromethyl, trifluoromethyl, dichloromethyl, dibromoethyl, 1-(3-methylimidazolyl)-methyl, 2- or 3-(5-carboxymethylthienyl)methyl, 2- or 3-(4-carbamoylthienyl)methyl, 2- or 3-(5-methylthienyl)methyl, 2- or 3-(5-methoxythienyl)methyl, 2- or 3-(4-chlorothienyl)-methyl, 2- or 3-(5-sulfothienyl)methyl, 2- or 3-(5-carboxythienyl)methyl, 3-(1,2,5-thiadiazolyl)methyl, 3-(4-methoxy-1,2,5-thiadiazolyl)methyl, 2-furylmethyl, 2-(5-nitrofuryl)methyl, 3-furylmethyl, 2-thienylmethyl, and tetrazolylmethyl. The term "sulfo" represents mercapto or thio, sulfinyl and sulfonyl.

The acyl group can also be a radical of the formula

wherein n is 0-4, Z represents oxygen, sulfur or nitrogen, and R" is defined as above. Representative members of the substituent

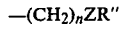

are allylthiomethyl, allylaminomethyl, phenylthiomethyl, butylmercaptomethyl, α-chlorocrotylmercaptomethyl, phenoxymethyl, phenylaminomethyl, phenoxyethyl, phenoxybutyl, phenoxybenzyl,, diphenoxymethyl, dimethylmethoxymethyl, dimethylbutoxymethyl, dimethylphenoxymethyl, 4-guanidinophenoxymethyl, 4-pyridylthiomethyl, p-(carboxymethyl)-phenoxymethyl, p-(carboxymethyl)phenylthiomethyl, 2-thiazolylthiomethyl, p-(sulfo)phenoxymethyl, p-(sulfo)phenylthiomethyl, p-(carboxy)phenoxymethyl, p-(carboxy)phenylthiomethyl, p-(carboxymethyl)phenoxymethyl, p-carboxymethyl)phenylthiomethyl, 2-pyrimidinylthiomethyl, phenethylthiomethyl, 1-(5,6,7,8-tetrahydronaphthyl)oxomethyl, 6,8-bis(methylthio)octanoyl.

Furthermore, the acyl group can be a radical of the formula

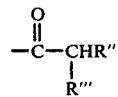

wherein R" is defined as above and R'" is a radical such as amino, hydroxy, azido, carbamoyl, guanidino, alkanoyloxy, halo, sulfamino, tetrazolyl, sulfo, carboxy, carbalkoxy, and the like. Representative members of the substituent

are α-aminobenzyl, α-amino-2-thienyl, α-methylaminobenzyl, α-amino-γ-methylmercaptopropyl, α-amino-3 or 4-chlorobenzyl, α-amino-3 or 4-hydroxybenzyl, α-amino-2,4-dichlorobenzyl, α-amino-3,4-dichlorobenzyl, D(−)-α-hydroxybenzyl, α-carboxybenzyl, α-amino-3-thienyl, α-amino-2-thienyl, D(−)-α-amino-3-chloro-4-hydroxybenzyl, D(−)-α-amino-3-thienyl, 1-aminocyclohexyl, α-(5-tetrazolyl)benzyl, α-sulfaminobenzyl, α-sulfamino-3-thienyl, α-(N-methylsulfamino)benzyl, D(−)-α-guanidino-2-thienyl, D(−)-α-guanidinobenzyl, α-guanylureidobenzyl, α-hydroxybenzyl, α-azidobenzyl, α-fluorobenzyl, 4-(5-methoxy-1,3-oxadiazolyl)-aminomethyl, 4-(5-methoxy-1,3-oxadiazolyl)-hydroxymethyl, 4-(5-methoxy-1,3-oxadiazolyl)-carboxymethyl, 4-(5-methoxy-1,3-sulfadiazolyl)-aminomethyl, 4-(5-methoxy-1,3-sulfadiazolyl)-hydroxymethyl, 4-(5-methoxy-1,3-sulfadiazolyl)-carboxymethyl, 2-(5-chlorothienyl)-aminomethyl, 2-(5-chlorothienyl)hydroxymethyl, 2-(5-chlorothienyl)-carboxymethyl, 3-(1,2-thiazolyl)aminomethyl, 3-(1,2-thiazolyl)hydroxymethyl, 3-(1,2-thiazolyl)-carboxymethyl, 2-(1,4-thiazolyl)aminomethyl, 2-(1,4-thiazolyl)-hydroxymethyl, 2-(1,4-thiazolyl)-carboxymethyl, 2-benzothienylaminomethyl, 2-benzothienylhydroxymethyl, 2-benzothienylcarboxymethyl, 2-azidooctyl-3-phenyl-3-azidomethyl, α-sulfobenzyl, and α-phosphonobenzyl.

Alternatively, the group

can be an unsubstituted or substituted alkyl or aryl sulfonamido group such as phenylsulfonamido, ethylsulfonamido, trifluoromethane sulfonamido, benzylsulfonamido, 2,5-dimethylsulfonamido, 4-chlorophenylsulfonamido, 4-methoxyphenylsulfonamido, and the like.

Preferably, R' is:
(1) hydrogen;
(2)

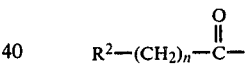

where $R^2$ represents:
(a) hydrogen;
(b) methyl or substituted methyl such as trifluoromethyl, cyanomethyl a methoxymethyl;
(c) thienyl;
(d) phenyl; or
(e) mono- and disubstituted phenyl and thienyl wherein the substituents are selected from the group consisting of chloro, bromo, fluoro, nitro, loweralkyl, and loweralkoxy;
n is 0 or 1; or
(3)

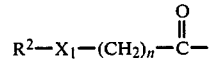

where
$X_1$ is oxygen or sulfur;
$R^2$ and n are as previously defined.
Even more preferably, R' is

$R^2$ being selected from the group consisting of:

(1) trifluoromethyl;
(2) methyl;
(3) methoxy;
(4) hydrogen;
(5) benzyl;
(6) phenyl;
(7) 2-thienylmethyl;
(8) phenylthiomethyl;
(9) phenoxymethyl;
(10) benzyloxy, or
(11) $NCCH_2SCH_2$.

Furthermore, $R_1$ in formula (I) above represents a nitrogen bonded group such as amino, substituted amino groups, nitro, azido, nitroso, isocyanato, isothiocyanato and hydroxyamino. Specific examples of nitrogen bonded groups that might be mentioned are $-N_3$, $-NH_2$, $-NHR_2$, $NR_2R_3$, wherein $R_2$ represents a straight or branched chain loweralkyl group of 1 to 6 carbon atoms, $R_3$ represents $R_2$ or hydrogen, and n represents the integer 1 or 2.

B of Formula (I) above represents $OB_1$, or $NB_2B_3$ wherein $B_1$ and $B_2$ independently are hydrocarbyl or substituted hydrocarbyl which can be loweralkyl, loweralkenyl alkyl, alkanoyl, alkanoylalkyl, alkanoyloxyalkyl, alkoxyalkyl, loweralkynyl, aralkyl, aryl, and cycloalkyl, a heterocyclic group, such as heterocyclic alkyl or heterocyclic alkenyl which can also be substituted with one or more groups such as halo (Cl, F, Br, etc.) hydroxy, alkoxy, mercapto, amino, substituted amino, nitro, sulfonyl, sulfinyl, sufamoyl, alkanoyloxy, carbamoyloxy, carboxy, alkanoyl carboxamido and N-substituted carboxamido; and $B_3$ is hydrogen or $B_1$.

Preferably $B_1$ and $B_2$ independently are substituted or unsubstituted
(1) aralkyl;
(2) aryl;
(3) straight or branched loweralkyl;
(4) straight or branched loweralkenyl;
(5) cycloalkyl;
(6) alkanoyloxyloweralkyl;
(7) alkanoylloweralkyl;
(8) alkoxyloweralkyl; or
(9) haloalkyl; and
$B_3$ is hydrogen or $B_1$.

Representative examples of such groups are $C_{1-6}$alkyl especially methyl, ethyl or t-butyl, allyl, 3-butenyl, methoxyethyl, benzyl, p-carbomethoxybenzyl, m-carbomethoxybenzyl, p-sulfonylbenzyl, m-fluorobenzyl, o,p-dinitrobenzyl, o,p-dichlorobenzyl, p-methylbenzyl, p-methoxybenzyl, o-methylthiobenzyl, benzhydryl, $-CH_2CH_2CH_2COOCH_3$, $-CH_2COOC_2H_5$, and the like.

More preferably, $B_1$ and $B_2$ independently are substituted or unsubstituted
(1) benzyl;
(2) ethyl;
(3) t-butyl;
(4) $-CH_2CH_2CH=CH_2$; or $-CH_2CH=C(CH_3)_2$;
(5) $-CH_2CH_2CH_2COOt-Bu$;
(6) alkanoyloxymethyl; or
(7) alkanoylmethyl; and
$B_3$ is hydrogen or $B_1$.

Q in formula (I) represents:
(1) hydrogen;
(2) $C_{1-6}$ especially methyl, ethyl, isopropyl, n-pentyl and n-hexyl,
(3) halo $C_{1-6}$alkyl especially chloro or fluoro $C_{1-6}$alkyl; or (4) hydroxy $C_{1-6}$alkyl;
(5) methylene or substituted methylene especially $C_{1-6}$alkylmethylene, unsubstituted or substituted phenylmethylene, phenylthiomethylene, phenylsulfinylmethylene or phenyl sulfonyl methylene;
(6) $C_{1-6}$alkoxy, $C_{1-6}$alkyl;
(7) unsubstituted or substituted benzyl; or
(8) unsubstituted or substituted phenylthio$C_{1-6}$ alkyl, phenylsulfonyl$C_{1-6}$alkyl,
(9) unsubstituted or substituted phenoxy$C_{1-6}$alkyl or
(10) unsubstituted or substituted phenylamino$C_{1-6}$alkyl.

Preferably, Q is:
(1) hydrogen;
(2) $C_{1-6}$ alkyl;
(3) substituted or unsubstituted methylene;
(4) unsubstituted or substituted phenylthio$C_{1-6}$alkyl or phenylsulfonyl$C_{1-6}$alkyl.

Even more preferably, Q is:
(1) hydrogen;
(2) methyl, ethyl or i- or n-propyl;
(3) methylene; or
(4) phenylthiomethyl or phenylsulfonylmethyl.

The cephalosporin sulfone esters of structural formula (I) where $OB_1$ is other than hydroxy can be prepared from the corresponding acid according to conventional methods of esterification. For example, (1) A compound of formula (I) is treated with a lower alkanol, for example, methanol or ethanol in the presence of a catalyst such as any one or a combination of those illustrated below in Table I.

TABLE I

Catalysts for Esterification (1) Hydrochloric acid or hydrobromic acid
(2) Sulfuric acid
(3) $C_{1-3}$alkanoic acid e.g. acetic acid
(4) Phosphoric acid
(5) Trifluoroacetic acid or anhydride
(6) Trichloroacetic acid
(7) p-Toluenesulfonic acid or other arylsulfonic acids
(8) Acidic ion-exchange resins with calcium sulfate
(9) Polymer-protected aluminum chloride, e.g., a complex between anhydrous aluminum chloride and polystyrene-divinyl benzene copolymer diphenylphosphitepyridine
(10) A Lewis acid such as boron trifluoride
(11) Aromatic sulfonylchloride-pyridine, e.g., p-toluenesulfonylchloride
(12) triphenylphosphine ditriflate
(13) dicyclohexylcarbodiimide (DCCD)
(14) β-trichloromethyl-β-pro-piolactone
(15) N,N'-carbonyldimidazole
(16) triphenylphosphinediethylazodicarbonylate
(17) 6-chlorobenzensulfonyloxybenzotriazole
(18) 1-methyl-2-halopyridinium iodide-tertiary amine (e.g., triethylamine).

at from about 0° to about 150° C. with or without refluxing until the esterification is substantially complete. Optionally, a solvent may be used to facilitate the reaction. The common solvents used are benzene, toluene, xylene, sulfolane-xylene, methylene chloride, diethylether, tetrahydrofuran, 1,2-dimethoxyethane, dioxane and the like;

(2) A compound of formula (I) is converted to an acid halide such as acid chloride or bromide via treatment with a halogenating agent such as thionyl chloride, phosphorus penta- or oxychloride followed by reaction with an appropriate alcohol; and (3) Other methods such as alkylation of carboxylate salts (e.g., $K^+$, $Na^+$, $Ca^{++}$, $Ag^+$, $Cu^+$, tetralkylammonium-$R_4N^+$, and $Hg^{++}$ salts) of formula (I) with alkyl halides, for example, benzylchloride, benzyhydryl chloride; reaction with alkyl isoureas; treatment with diazomethane or diazophenylmethane ($N_2=CHC_6H_5$); alcoholysis of an anhydride derived from the cephalosporin acid corresponding to formula (I); transesterification with t-butyl esters or isopropenyl acetates and the like may also be used. These methods are disclosed in Saul Patai, editor, *The Chemistry of Functional Groups*, Supplement B, *The Chemistry of Acid Derivatives*, pp. 411–436, John Wiley & Sons, Chichester-New York-Brisbane-Toronto, 1979, and are incorporated herein by reference.

More specifically the following synthetic schemes are useful in preparing the cephalosporin sulfone esters or amides:

(1) As exemplified by Example 1

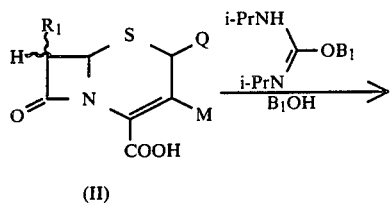

(II)

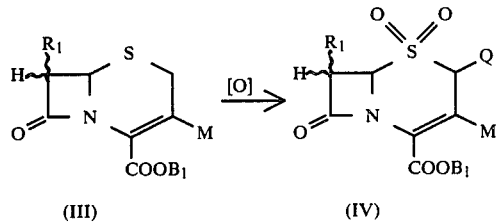

(III)     (IV)

wherein $B_1$ represents $C_{1-6}$alkyl such as methyl, ethyl or i- or n-propyl.

(2) As exemplified by Example 2

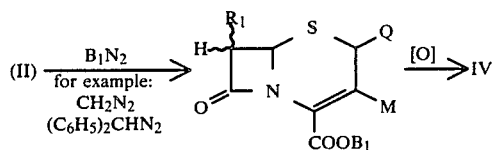

(3) As exemplified by Example 3

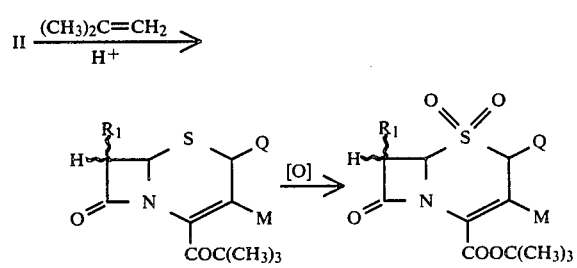

(4) Displacement Method

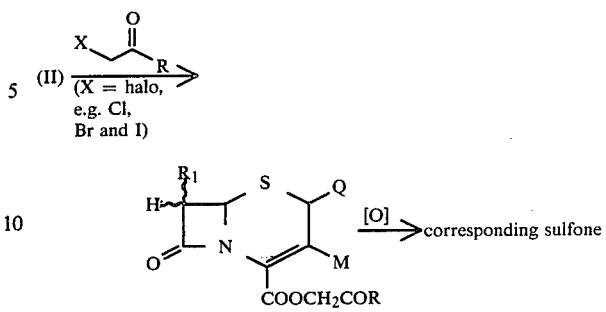

(5) Mixed Anhydride Method

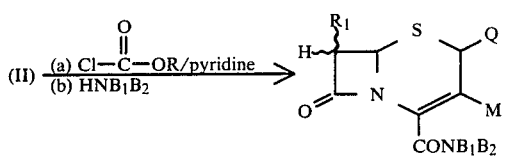

(6) DCC Coupling Method

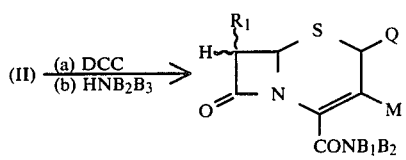

It should be noted that when it is appropriate, II can be oxidized first to a sulfone and then subject to esterification or amidation according to schemes (1) to (6).

The starting compound of formula (II) wherein Q is H and methods for the preparation thereof are known in most cases as they are known antibiotics and have been explored extensively. The following schemes, however, depict the preparation for a few exceptions:

(1) As exemplified in Example 5

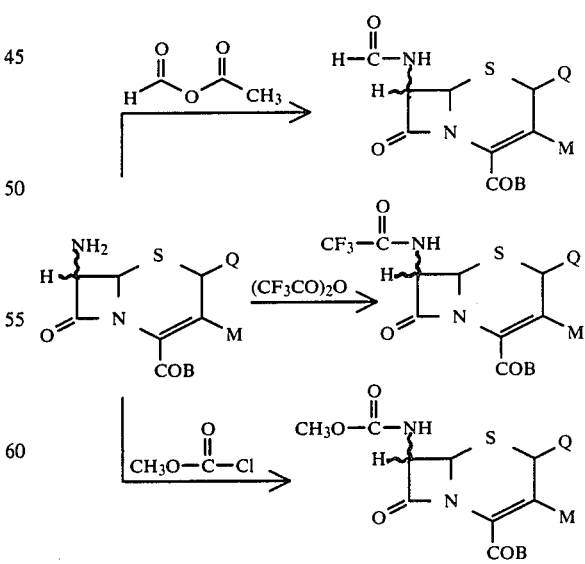

(2) Modification of the 2-position (introduction of substituent Q) as described in copending application, filed May 2, 1983, Ser. No. 490,761.

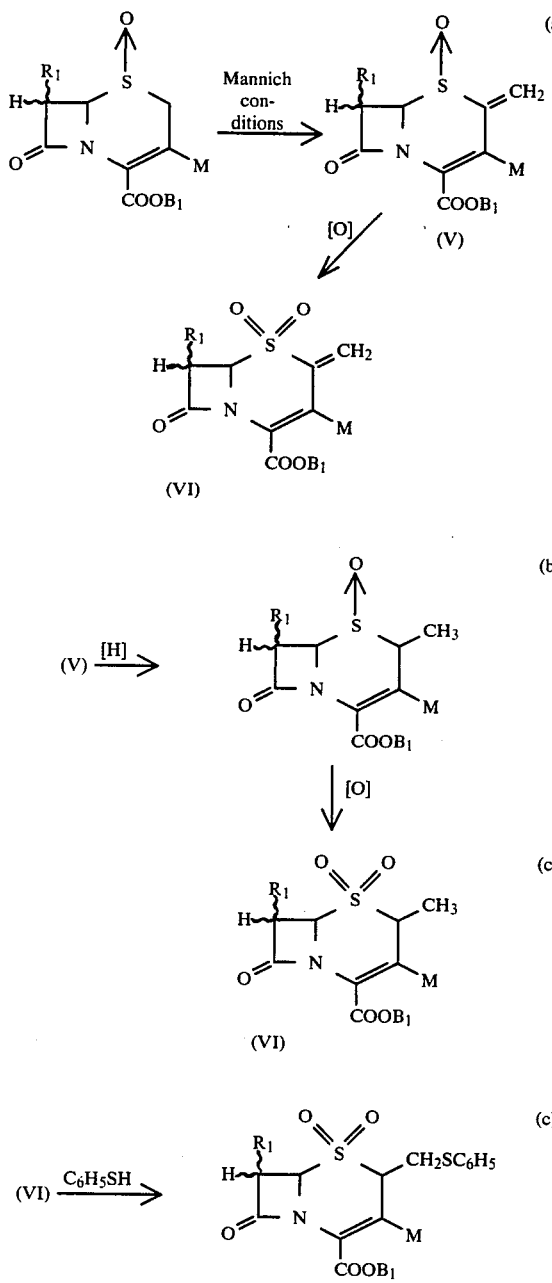

This invention also relates to a method of treating inflammation in patients using a compound of Formula (I), particularly an especially preferred compound as the active constituent.

It has been found that the compounds of Formula (I) have anti-inflammatory antidegeneration activity and are effective in the prevention and inhibition of edema and granuloma tissue formation as shown below in Table II by the effective inhibition of the proteolytic function of human granulocyte elastase.

TABLE II

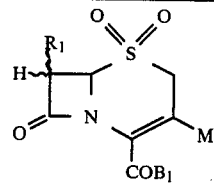

| $R_1$ | M | $B_1$ | $ED_{50}$ |
|---|---|---|---|
| —NHCOOCH$_3$ | CH$_2$OCOCH$_3$ | —OCH$_2\phi$* | 0.3 |
| —NHCOCF$_3$ | CH$_2$OCOCH$_3$ | —OCH$_2\phi$ | 0.04 |
| CF$_3$CONH— | —CF$_3$ | —OCH$_2\phi$ | 0.03 |
| CF$_3$CONH— | —CF$_3$ | —OtBu | 0.8 |

$\phi$* is C$_6$H$_5$(phenyl).

Protocol—Enzyme Assays for the Inhibition of Human Polymorphonuclear Leukocyte Elastase Via Hydrolysis of N-t-Boc-alanyl-alanyl-prolylalanine-p-nitroanilide Reagents 0.05M TES (N-tris[hydroxymethyl]methyl-2-aminoethanesulfonic acid) Buffer, pH 7.5.

0.2 mM N-t-Boc-alanyl-alanyl-prolyl-alanine-p-nitroanilide (Boc-AAPAN).

To prepare substrate, the solid (m.w. 550) was first dissolved in 10.0 ml DMSO. Buffer at pH 7.5 was then added to a final volume of 100 ml.

Crude extract of human polymorphonuclear leukocytes (PMN) containing elastase activity.

Inhibitors (cephalosporin sulfone esters) to be tested dissolved in DMSO just before use.

Assay Procedure

To 1.0 ml of 0.2 mM Boc-AAPAN in a cuvette, 0.01–0.1 ml of DMSO with or without inhibitor was added. After mixing, a measurement was taken at 410 m$\mu$ to detect any spontaneous hydrolysis due to presence of test compound. 0.05 Milliliters of PMN extract was then added and the $\Delta$OD /min at 410 m$\mu$ was measured and recorded. Beckman model 35 spectrophotometer was used.

Results

Results were reported as $ED_{50}$, i.e., effective dosage in micrograms per milliliter ($\mu$g/ml) for 50% inhibition of the enzyme activity 2 minutes after zero time.

Comments

The elastase activity in the crude PMN extract may vary from one preparation to another. A control of each new batch is run, and the volume added in the assay procedure is adjusted according to activity.

Accordingly, the compounds of Formula (I) can be used to reduce inflammation and relieve pain in diseases such as emphysema, rheumatoid arthritis, osteoarthritis, gout, bronchial inflammation, infectious arthritis, rheumatic fever and the like.

For treatment of inflammation, fever or pain, the compounds of Formula (I) may be administered orally, topically, parenterally, by inhalation spray or rectally in dosage unit formulations containing conventional nontoxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, maize starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or koalin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyxyethylene sorbitan monooleate. The said aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the anti-inflammatory agents are employed.

Dosage levels of the order to 0.2 mg to 140 mg per kilogram of body weight per day are useful in the treatment of the above-indicated conditions (10 mg to 7 gms. per patient per day). For example, inflammation is effectively treated and anti-pyretic and analgesic activity manifested by the administration from about 0.5 to 50 mg of the compound per kilogram of body weight per day (25 mg to 3.5 gms per patient per day). Advantageously, from about 2 mg to about 20 mg per kilogram of body weight per daily dosage produces highly effective results (50 mg to 1 gm per patient per day).

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

EXAMPLE 1

Benzyl 3-acetyloxymethyl-7α-trifluoromethylcarbonylamino-8-oxo-5-thia-1-azabicyclo[4.2.0]oct-2-ene-2-carboxylate-5,5-dioxide Step A: Preparation of 3-acetyloxymethyl-7α-trifluoromethylcarbonylamino-8-oxo-5-thia-1-azabicyclo[4.2.0]oct-2-ene-2-carboxylic acid To 0.1519 g of t-butyl 3-acetyloxymethyl-7α-trifluoromethylcarbonylamino-8-oxo-5-thia-1-azabicyclo[4.2.0]oct-2-ene-2-carboxylate was added 3 ml of trifluoroacetic acid with stirring at room temperature. After 15 minutes of stirring, the mixture was concentrated to dryness under a stream of nitrogen to give 3-acetyloxymethyl-7α-trifluoromethylcarbonylamino-8-oxo-5-thia-1-azabicyclo[4.2.0]oct-2-ene-2-carboxylic acid as an amber oil which was used in the next step without further purification.

Step B: Preparation of Benzyl 3-acetyloxymethyl-7α-trifluoromethylcarbonylamino-8-oxo-5-thia-1-azabicyclo[4.2.0]oct-2(and 3)-ene-2-carboxylate A mixture of 0.1318 gms of crude 3-acetyloxymethyl-7α-trifluoromethylcarbonylamino-8-oxo-5-thia-1-azabicyclo[4.2.0]oct-2-ene-2-carboxylic acid and 0.2516 gms of N,N'-diisopropyl-0-benzylisourea in 10 ml of dichloromethane was stirred at room temperature for 40 hours. The resulting mixture was concentrated to dryness under reduced pressure. The residue was purified by chromatography on silica gel using 50:50 hexane:ethyl acetate as the eluting solvent to give 0.1262 g of a yellow oil (77% yield) consisting of a 26:74 ratio of 2-ene:3-ene isomers (by NMR) of Benzyl 3-acetyloxymethyl-7α-trifluoromethylcarbonylamino-8-oxo-5-thia-1-azabicyclo[4.2.0]oct-2(and 3)-ene-2-carboxylate.

Step C: Preparation of Benzyl 3-acetyloxymethyl-7α-trifluoromethylcarbonylamino-8-oxo-5-thia-1-azabicyclo[4.2.0]oct-2-ene-2-carboxylate-5,5-dioxide In a round bottom flask were placed 0.1262 gms of benzyl 3-acetyloxymethyl-7α-trifluoromethylcarbonylamino-8-oxo-5-thia-1-azabicyclo[4.2.0]oct-2(and 3)-ene-2-carboxylate and 20 ml of methylene chloride. The resulting mixture was stirred under nitrogen with ice bath cooling, then meta-chloroperbenzoic acid (0.1230 g, 80–90% pure) was added, the ice bath was removed, and stirring was continued for seventy hours. The reaction mixture was diluted with ethyl acetate, and washed with saturated sodium sulfite, saturated sodium bicarbonate and then saturated brine. The organic layer was dried over MgSO$_4$, and concentrated to give a crude product. This product was purified by column chromatography on silica gel using hexane:ethyl acetate (1:1) to give 0.1015 gms of benzyl 3-acetyloxy-methyl-7α-trifluoromethylcarbonylamino-8-oxo-5-thia-1-azabicyclo[4.2.0]oct-2-ene-2-carboxylate-5,5-dioxide as a white solid, m.p. 148°–150.5° C.

EXAMPLE 2

Methyl 3-acetyloxymethyl-7α-trifluoromethylcarbonylamino-8-oxo-5-thia-1-azabicyclo[4.2.0]oct-2-ene-2-carboxylate-5,5-dioxide A diazomethane solution was prepared from 3.0 gms of N-methyl-N-nitrosourea in 30 ml of ether over an aqueous solution containing 6.0 gms of potassium hydroxide at 0° C. for 1 hour. The bright yellow organic phase was then dried over potassium hydroxide pellets for 15 minutes, and decanted into a solution containing 0.826 gms of 3-acetyloxymethyl-7α-trifluoromethylcarbonylamino-8-oxo-5-thio-1-azabicyclo[4.2.0]-2-ene-2-carboxylic acid in 25 ml of ether at 0° C. After stirring for 1 hour, with ice bath cooling, the excess diazomethane was decomposed by careful dropwise addition of glacial acetic acid until nitrogen evolution ceased. The mixture was then washed successively with portions of 10% aqueous acetic acid, water, saturated sodium bicarbonate solution, and water. Drying over magnesium sulfate, filtration, removal of solvent under reduced pressure and filtration of the residue through a 1 inch plug of silica gel in a 6 ml sintered glass funnel using 500 ml of 80:20 dichloromethane:ether gave 0.5489 gm (yield 74%) of methyl 3-acetyloxymethyl-7α-trifluoromethylcarbonylamino-8-oxo-5-thia-1-azabicyclo[4.2.0]oct-2-ene-2-carboxylate as a yellow oil which was subsequently oxidized as described in Example 1, Step C to afford 0.334 g (56%) of methyl 3-acetyloxymethyl-7α-trifluoromethylcarbonylamino-8-oxo-5-thia-1-azabicyclo[4.2.0]oct-2-ene-2-carboxylate-5,5-dioxide, m.p. 172°–173.5° C.

EXAMPLE 3 t-Butyl 3-methyl-7β-amino-8-oxo-5-thia-1-azabicyclo[4.2.0]oct-2-ene-2-carboxylate To a solution of 2.5 ml of sulfuric acid in 25 ml of dioxane were added, with ice cooling, 2.5 g (11.7 mmol) of 3-methyl-7β-amino-8-oxo-5-thia-1-azabicyclo[4.2.0]oct-2-ene-2-carboxylic acid and 15 ml of isobutylene. The mixture was sealed in a pressure bottle and stirred for 2 hours at room temperature. The contents of the bottle were poured into 300 ml of ice-cold water containing 15 g of sodium bicarbonate. The solution was extracted with ethyl acetate. The combined ethyl acetate extract was washed with brine and dried over sodium sulfate. Evaporation of the filtrate in vacuo gave 1.2 g (38% yield) of t-butyl 3-methyl-7β-amino-8-oxo-5-thia-1-azabicyclo[4.2.0]oct-2-ene-2-carboxylate. NMR (CDCl$_3$): δ 1.51 (s, 9), 1.78 (bs, 2), 2.05 (s, 3), 3.3 (ABq, 2, 18 Hz), 4.64 (d, 1, 4 Hz), 4.85 (d, 1, 4 Hz).

EXAMPLE 4 t-Butyl 3-acetyloxymethyl-7β-formamido-8-oxo-5-thia-1-azabicyclo[4.2.0]oct-2-ene-2-carboxylate-5,5-dioxide To a solution of t-butyl 3-acetyloxymethyl-7β-amino-8-oxo-5-thia-1-azabicyclo[4.2.0]oct-2-ene-2-carboxylate (328 mg, 1.0 mmoles) in methylene chloride (10 ml) cooled to 0° under $N_2$ was added acetic-formic anhydride (200 μl). The cooling bath was removed and the mixture was stirred for one hour, then concentrated to a yellow oil. This oil was chromatographed (2×2000μ (20×20 cm) silica gel GF using ethyl acetate:hexane [1:1] as eluent). The band at $R_f=0.6$ was removed and eluted to give 234 mg (66%) of product as an oil which solidifies on standing.

Following the same procedures as described in Example 1, Step C, t-butyl 3-acetyloxymethyl-7β-formamido-8-oxo-5-thia-1-azabicyclo[4.2.0]oct-2-ene-2-carboxylate (130 mg, 0.37 mmol) was oxidized to give 119 mg of t-butyl 3-acetyloxymethyl-7β-formamido-8-oxo-5-thia-1-azabicyclo[4.2.0]oct-2-ene-2-carboxylate-5,5-dioxide. M.S. M+ (388) for $C_{15}H_{20}N_2SO_8$.

EXAMPLE 5 t-Butyl 3-acetyloxymethyl-7α-trifluoroacetamido-8-oxo-5-thia-1-azabicyclo[4.2.0]oct-2-ene-2-carboxylate-5,5-dioxide To a stirred solution of 2.00 gms of t-butyl 3-acetyloxymethyl-7-amino-8-oxo-5-thia-1-azabicyclo[4.2.0]oct-2-ene-2-carboxylate (epimeric mixture of 7α and 7β) in 150 ml dichloromethane was added 1.45 grams of pyridine followed by 3.84 gms of trifluoroacetic anhydride with cooling in an ice bath. The reaction was stirred for an additional 20 minutes with cooling, then poured into 50 ml of a saturated sodium bicarbonate solution and diluted with ethyl acetate. The layers were separated and the organic phase washed successively with 100 ml water, two 50 ml portions of 10% aqueous acetic acid, 100 ml water, two 50 ml portions of saturated sodium bicarbonate solution and three portions of water. Drying over magnesium sulfate, removal of solvent in vacuo and chromatography of the resulting epimeric mixture on silica gel using 75:25 hexane:ethyl acetate as the eluting solvent gave 0.835 gms of t-butyl 3-acetyloxymethyl-7α-trifluoroacetamido-8-oxo-5-thia-1-azabicyclo[4.2.0]oct-2-ene-2-carboxylate, mp=130°-132° C. (d).

Following substantially the same procedure as described in Example 1, Step C, 0.3987 gms of t-butyl 3-acetyloxymethyl-7α-trifluoroacetamido-8-oxo-5-thia-1-azabicyclo[4.2.0]oct-2-ene-2-carboxylate in 37.5 ml of dichloromethane was oxidized to give 0.3241 gms (76% yield) of t-butyl 3-acetyloxymethyl-7α-trifluoroacetamido-8-oxo-5-thia-1-azabicyclo[4.2.0]oct-2-ene-2-carboxylate-5,5-dioxide as a white solid, m.p.=170° C. (d). NMR (CDCl₃/DMSO): δ=1.54 (s, 9H), 2.06 (s, 3H), 3.71, 4.11 (ABq, J=18 Hz, 2H), 4.54, 4.89 (ABq, J=13.5 Hz, 2H), 5.19 (m, 2H), 9.98 (bd, J=7.2 Hz, 1H).

Following substantially the same procedures as described above but substituting for the trifluoroacetic anhydride used therein, methyl chloroformate (0.576 g), there was obtained from 1.0 g of t-butyl 3-acetyloxymethyl-7-amino-8-oxo-5-thia-1-azabicyclo[4.2.0]oct-2-ene-2-carboxylate 0.248 g of pure t-butyl 3-acetyloxymethyl-7α-methoxycarbonylamino-8-oxo-5-thia-1-azabicyclo[4.2.0]oct-2-ene-2-carboxylate, m.p. 168°-169.5° C. (d). This product was subsequently oxidized to t-butyl 3-acetyloxymethyl-7α-methoxycarbonylamino-8-oxo-5-thia-1-azabicyclo[4.2.0]oct-2-ene-2-carboxylate-5,5-dioxide (m.p. 154° C. dec.) according to procedures also described above in Example 1, Step C.

Furthermore, 1.06 g of the t-butyl 3-acetyloxymethyl-7α-methoxycarbonylamino-8-oxo-5-thia-1-azabicyclo[4.2.0]oct-2-ene-2-carboxylate obtained above was converted as in Example 1, Steps A and B to the corresponding benzyl ester (0.192 g) followed by oxidation to afford 0.137 g of benzyl 3-acetyloxymethyl-7α-methoxycarbonylamino-8-oxo-5-thia-1-azabicyclo[4.2.0]oct-2-ene-2-carboxylate-5,5-dioxide, m.p.=162°-164° C. (d). NMR (CDCl₃): δ 2.00 (s, 3H), 3.60 (bs, 3H), 3.63, 3.98 (ABq, J=17 Hz, 2H), 4.57, 4.87 (ABq, J=13.5 Hz, 2H), 5.00 (m, 2H, 5.23 (s, 2H), 5.93 (d, J=7.5 Hz, 1H), 7.27 (m, 5H).

EXAMPLE 6 t-Butyl 3-trifluoromethyl-7α-trifluoromethylcarbonylamino-8-oxo-5-thia-1-azabicyclo[4.2.0]oct-2-ene-2-carboxylate-5,5-dioxide Step A: Preparation of t-Butyl N-benzylideneglycinate To a solution of 33.61 gms of glycine t-butyl ester and 27.19 gms of benzaldehyde in 215 ml benzene was added 21.5 gms of magnesium sulfate in one portion with stirring at room temperature. The reaction was stirred 18 hours at room temperature, filtered, diluted with ether and washed with saturated sodium bicarbonate and brine. The ether solution was then dried over magnesium sulfate, concentrated and distilled to yield 48.41 gms (86%) of t-butyl N-benzylideneglycinate.

Step B: Preparation of (2R,3S) and (2S,3R)-t-Butyl 2-amino-4-bromo-3-hydroxy-3-trifluoromethylbutyrate To a stirred solution of 18.00 gm of t-butyl N-benzylideneglycinate in 165 ml dry tetrahydrofuran at −78° under nitrogen was added 48.0 ml of a 1.69M solution of n-butyl lithium in hexane dropwise over 10 minutes. After stirring an additional 10 minutes, 15.68 g of 3-bromo-1,1,1-trifluoropropanone was added dropwise, and the mixture allowed to warm gradually to −20° C. before it was recooled to −78° C. and quenched by addition of 4.70 ml glacial acetic acid. The reaction was then concentrated under reduced pressure to yield a residue which was partitioned between water and ether. The organic phase was separated, water washed, dried over magnesium sulfate, filtered and evaporated. The resulting brownish oil was taken up in 165 ml methanol and treated with 13.84 gms of Girard T reagent at room temperature for 1 hour. The solution was then concentrated to dryness and the residue shaken with water and ether. The layers were separated, and the organic phase washed with water, dried over magnesium sulfate, filtered and concentrated under reduced pressure to give 22.88 gms of a yellow oil which was chromatographed on silica gel, eluting with 90:10 hexane:ethyl acetate to yield (2R,3S) and (2S,3R)-t-Butyl 2-amino-4-bromo-3-hydroxy-3-trifluoromethylbutyrate as a yellow oil. NMR (CDCl₃): δ=1.51 (s, 9H), 3.31 (bs, 3H), 3.80 (s, 2H), 3.88 (d, J=1.1 Hz, 1H).

Step C: Preparation of (2R,3S) and (2S,3R)-t-Butyl 4-bromo-3-hydroxy-2-thioformamido-3-trifluoromethyl butyrate A solution of 11.36 gms of (2R,3S) and (2S,3R)-t-Butyl 2-amino-4-bromo-3-hydroxy-3-trifluoromethylbutyrate in 5 ml CCl$_4$ was combined with 3.97 gms of ethyl thionoformate and allowed to stir at room temperature for 18 hours. The reaction mixture was then concentrated under reduced pressure and purified by chromatography on silica gel using 80:20 hexane:ethyl acetate as the eluting solvent to yield 3.67 gms of (2R,3S) and (2S,3R)-t-butyl 4-bromo-3-hydroxy-2-thioformamido-3-trifluoromethylbutyrate NMR (CDCl$_3$): δ 1.53 (s, 9H), 3.67, 3.95 (AB-q, J=12 Hz, 2H), 4.13 (d, J=3 Hz, 1H), 6.06 (d, J=9 Hz, 1H), 8.22 (d, J=6 Hz, 1H), 9.48 (d, J=6 Hz, 1H).

Step D: Preparation of (4R,5S) and (4S,5R) t-Butyl 5-hydroxy-5-trifluoromethyl-4,5-dihydro-6H-1,3-thiazine-4-carboxylate To a solution of 3.67 gms of (2R,3S) and 2S,3R)-t-butyl 4-bromo-3-hydroxy-2-thioformamido-3-trifluoromethylbutyrate in 65 ml acetone was added 4.15 g powdered anhydrous potassium carbonate. The reaction mixture was stirred for 30 minutes at room temperature, filtered and evaporated to dryness under reduced pressure. The crude brown oil was then purified by chromatography on silica gel using 80:20 hexane:ethyl acetate as the eluting solvent to give 0.781 gms of white solid, (4R,5S) and (4S,5R)-t-butyl 5-hydroxy-5-trifluoromethyl-4,5-dihydro-6H-1,3-thiazine-4-carboxylate (yield 27%) m.p. 126.5°–127.5° C. NMR (CDCL$_3$): δ=1.55 (s, 9H), 2.93, 3.13 (AB-q, J=13.8 Hz, 2H), 4.13 (d, J=2.7 Hz, 1H), 5.33 (s, 1H), 8.25 (d-d, J=2.7, 1.2 Hz, 1H).

Step E: Preparation of t-Butyl 3-trifluoromethyl-7α-azido-8-oxo-5-thia-1-azabicyclo[4.2.0]-oct-2(or 3)-ene-2-carboxylate Into an oven dried 3-necked round bottom flask equipped with a magnetic stirrer, addition funnel, drying tube and nitrogen inlet was weighed 0.1586 gms of a 50% mineral oil dispersion of sodium hydride under nitrogen. The sodium hydride was then washed with two 4 ml portions of hexane which were removed by pipet, then slurried in 14 ml dry tetrahydrofuran, cooled to 0° C. in an ice bath and treated with 0.8570 g (4R,5S) and (4S,5R)-t-butyl 5-hydroxy-5-trifluoromethyl-4,5-dihydro-6H-1,3-thiazine-4-carboxylate in 9.3 ml tetrahydrofuran dropwise over 5–10 minutes. The reaction was stirred an additional 15 minutes before 0.3785 g of methanesulfonyl chloride was added dropwise via syringe in 0.2 ml tetrahydrofuran. After 2 hours of stirring at 0° C., the mixture was cooled to −78° C., and 0.3344 g of triethylamine was added in one portion followed by dropwise addition of 0.3590 g neat azidoacetyl chloride. The reaction mixture was then allowed to warm slowly to room temperature over a 2½ hour period, after which it was poured into water and extracted with ethyl acetate. The organic phase was then washed with 2N hydrochloric acid solution, saturated sodium bicarbonate solution and water. Drying over magnesium sulfate followed by filtration and removal of solvent in vacuo yields 1.349 g of yellow oil which was dissolved in 25 ml dry pyridine under nitrogen and placed in an 83° C. oil bath with stirring for 40 minutes. The solution was then cooled and poured into water-ethyl acetate. An aqueous 10% KHSO$_4$ solution was then added until the aqueous phase is acidic, the layers are then separated, and the ethyl acetate solution was washed with water, dried over magnesium sulfate, filtered, and evaporated under reduced pressure to give a crude brown oil which was purified by elution through 9 gms of silica gel with 300 ml dichloromethane to afford 0.8849 g (84%) of a yellow oil consisting of a variable ratio of 2-ene- and 3-ene-isomers of t-butyl 3-trifluoromethyl-7α-azido-8-oxo-5-thia-1-azabicyclo[4.2.0]-2(or 3)-ene-2-carboxylate (CDCl$_3$): δ=1.57 (s, 9H), 3.33, 3.58 (AB-q, J=17.7 Hz, 2H), 4.60, 4.64 (AB-q, J=2.3 Hz, 2H). (spectrum of pure 2-ene-isomer).

Step F: Preparation of t-Butyl 3-trifluoromethyl-7α-amino-8-oxo-5-thia-azabicyclo[4.2.0]oct-2(or 3)-ene-2-carboxylate A solution containing 9.3 mgs of t-butyl 3-trifluoromethyl-7α-azido-8-oxo-5-thia-1-azabicyclo[4.2.0]-2(or 3)-ene-2-carboxylate and 5.5 mgs of platinum oxide in 3 ml of ethyl acetate was shaken for 1 hour under 35 psi hydrogen in a Parr shaker. A second portion of 5.1 mg of platinum oxide was then added, and the reaction was shaken another 30 minutes before it was judged complete by thin layer chromatography, filtered through celite and concentrated to give 8.3 mgs (96%) of t-butyl 3-trifluoromethyl-7α-amino-8-oxo-5-thia-azabicyclo[4.2.0]oct-2(or 3)-ene-2-carboxylate as a dark residue which was used without further purification.

Step G: t-Butyl 3-trifluoromethyl-7α-trifluoromethylcarbonylamino-8-oxo-5-thia-1-azabicyclo[4.2.0]oct-2-ene-2-carboxylate-5,5-dioxide Following the same procedure as described in Example 5, 8.3 mg. of t-butyl 3-trifluoromethyl-7α-amino-8-oxo-5-thia-azabicyclo[4.2.0]oct-2(or 3)-ene-2-carboxylate was converted first to 8.8 mg of t-butyl 3-trifluoromethyl-7α-trifluoromethylcarbonylamino-8-oxo-5-thia-1-azabicyclo[4.2.0]oct-2-(or 3)ene-2-carboxylate (81%), NMR (CDCl$_3$): δ=1.47 (s, 9H), 4.97 (m, 3H), 6.96 (s, 1H), 7.42 (m, 1H), and then oxidized to 8.3 mg of t-butyl 3-trifluoromethyl-7α-trifluoromethylcarbonylamino-8-oxo-5-thia-1-azabicyclo[4.2.0]oct-2-ene-2-carboxylate-5,5-dioxide (87% yield). m.p.=255° C. (d), NMR (CDCl$_3$/DMSO): δ=1.53 (s, 9H), 3.58, 4.16 (AB-q, J=17 Hz, 2H), 5.33 (m, 2H), 9.98 (m, 1H).

EXAMPLE 7

Following the procedures described in (1) Example 1, Step B and (2) Example 6, Step G and/or Example 5, the following derivatives were prepared.

(1) Benzyl 3-trifluoromethyl-7α-trifluoromethylcarbonylamino-8-oxo-5-thia-1-azabicyclo[4.2.0]oct-3-ene-2-carboxylate, NMR (CDCl$_3$): δ=4.93 (m, 2H), 5.13 (s, 3H), 7.00 (m, 1H), 7.28 (s, 5H), 7.68 (bd, J=7 Hz, 1H).

(2) Benzyl 3-trifluoromethyl-7α-trifluoromethylcarbonylamino-8-oxo-5-thia-1-azabicyclo[4.2.0]oct-2-ene-2-carboxylate-5,5-dioxide, NMR (CDCl$_3$/DMSO): δ3.65; 4.22 (AB-q, J=17.7 Hz, 2H); 5.24 (m, 2H); 5.39 (m, 2H), 7.33 (s, 5H), 9.97 (bd, J=7.2 Hz, 1H).

(3) Benzyl 3-trifluoromethyl-7α-methoxycarbonylamino-8-oxo-5-thia-1-azabicyclo[4.2.0]oct-2-ene-2-carboxylate-5,5-dioxide.

(4) Benzyl 3-trifluoromethyl-7α-formamido-8-oxo-5-thia-1-azabicyclo[4.2.0]oct-2-ene-2-carboxylate-5,5-dioxide.

EXAMPLE 8 p-Methoxybenzyl or Benzyl 3-methyl-7α-azido (or trifluoromethylcarbonylamino, or methoxycarbonylamino)-8-oxo-5-thia-1-azabicyclo[4.2.0]oct-2-ene-2-carboxylate-5,5-dioxide Step A: Preparation of p-Methoxybenzyl 3-methyl-7α-azido-8-oxo-5-thia-1-azabicyclo[4.2.0]oct-2-ene-2-carboxylate A solution containing 3.42 grams of p-methoxybenzyl 5-methyl-6H-1,3-thiazine-4-carboxylate in 120 ml of dichloromethane was cooled in a dry ice-acetone bath. To the above stirred solution was then added 1.35 gms of triethylamine in one portion, followed by 1.59 gms of azidoacetyl chloride in 20 ml of dichloromethane dropwise over 5 minutes. Following the additions, the reaction mixture was allowed to remain in the cooling bath to come to room temperature overnight. After stirring 18 hours, the reaction mixture was washed with two 200 ml portions of water, dried over magnesium sulfate, filtered, concentrated and the residue purified by chromatography or silica gel using an 80:20 hexane:ethyl acetate mixture as the eluting solvent. Yield=2.89 gms (60%) of p-Methoxybenzyl 3-methyl-7α-azido-8-oxo-5-thia-1-azabicyclo[4.2.0]oct-2-ene-2-carboxylate as amber oil. NMR (CDCl$_3$): δ=2.06 (s, 3H), 3.08, 3.45 (AB-q, J=17 Hz, 2H), 3.77 (s, 3H), 4.40 (d, J=2 Hz, b 1H), 4.50 (d, J=2 Hz, 1H), 5.05, 5.21 (AB-q, J=11 Hz, 2H), 7.02 (m, 4H).

Step B: Preparation of 3-Methyl-7α-azido-8-oxo-5-thia-1-azabicyclo[4.2.0]oct-2-ene-2-carboxylic acid To a solution of 2.759 gms of p-Methoxybenzyl 3-methyl-7α-azido-8-oxo-5-thia-1-azabicyclo[4.2.0]oct-2-ene-2-carboxylate in 49.5 ml of anisole under nitrogen was added 14.65 gms of trifluoroacetic acid at room temperature. The reaction was then stirred 90 minutes, poured into 200 ml of ice water containing 11.91 gms of sodium bicarbonate and extracted with three 200 ml portions of ether. The aqueous solution was then acidified (pH=3) by addition of 9.8 ml of 2N hydrochloric acid solution and extracted with three portions of ethyl acetate. The combined organic phases were then washed with three portions of brine, dried over magnesium sulfate and concentrated under reduced pressure to give 1.578 gms (86% yield) of 3-methyl-7α-azido-8-oxo-5-thia-1-azabicyclo[4.2.0]oct-2-ene-2-carboxylic acid as a tan solid, NMR (CDCl$_3$/DMSO): δ=2.12 (s, 3H), 3.11, 3.43 (AB-q, J=18 Hz, 2H), 4.44 (d, J=2 Hz, 1H), 4.53 (d, J=2 Hz, 1H), 11.0 (bs, 1H), which was further converted to the corresponding benzyl ester followed by oxidation to afford benzyl 3-methyl-7α-azido-8-oxo-5-thia-1-azabicyclo[4.2.0]oct-2-ene-2-carboxylate-5,5-dioxide, NMR (CDCl$_3$): δ=2.02 (s, 3H), 3.57, 3.85 (ABq, J=18 Hz, 2H), 4.56 (bs, 1H), 5.13 (d, J=2 Hz, 1H), 5.23 (s, 2H), 7.33 (s, 5H).

Following substantially the same procedures as described in Example 6, Steps F and G, there were prepared:

(1) Benzyl 3-methyl-7α-trifluoroacetamido-8-oxo-5-thia-1-azabicyclo[4.2.0]oct-2-ene-2-carboxylate-5,5-dioxide, m.p. 192°-194° C.; and (2) Benzyl 3-methyl-7α-methoxycarbonylamino-8-oxo-5-thia-1-azabicyclo[4.2.0]oct-2-ene-2-carboxylate-5,5-dioxide.

Following substantially the same procedures as described in (1) Example 1, Step C and (2) Example 6, Step F, there was prepared benzyl 3-methyl-7α-amino8-oxo-5-thia-1-azabicyclo[4.2.0]oct-ene-2-carboxylate-5,5-dioxide.

What is claimed is:

1. A pharmaceutical composition for treating and managing inflammatory conditions in mammalian species comprising a non-toxic pharmaceutical carrier and an effective amount of a compound of structural formula:

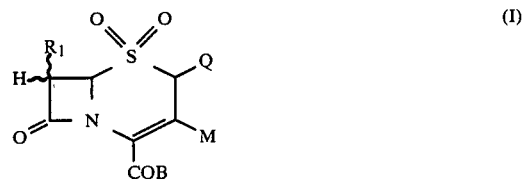

wherein M is:
(1) trifluoromethyl;
(2) chloro or fluoro;
(3) —COOH;
(4) —CHO; or
(5) —CH$_2$A wherein A represents
  (a) hydrogen;
  (b) halo;
  (c) hydroxy;
  (d) C$_{1-6}$alkoxy;
  (e) —O-phenyl or —O-substituted phenyl wherein the phenyl is substituted with one or more functional groups selected from a group consisting of C$_{1-6}$alkyl, C$_{1-6}$alkoxy, C$_{1-6}$alkylthio, C$_{1-6}$alkanoyl, C$_{1-6}$alkanoyloxy; nitro, C$_{1-6}$alkylamino, amino, halo, CF$_3$, CF$_3$S—, C$_{1-6}$alkylsulfinyl and C$_{1-6}$alkylsulfonyl;
  (f) —OCH$_2$phenyl or —OCH$_2$-substituted phenyl wherein the substituted phenyl is as previously defined;
  (g)

wherein R$_5$ is C$_{1-6}$alkyl, phenyl, substituted phenyl, —CH$_2$-phenyl or —CH$_2$-substituted phenyl; n is an integer of 0-2;
  (h) —S—COR$_5$;
  (i) C$_{1-6}$alkanoyloxy;
  (j) phenylcarbonyloxy;
  (k) —NH$_2$, —NHC$_{1-6}$alkyl, or —N(C$_{1-6}$alkyl)$_2$;
  (l) —CONH$_2$, —CONHC$_{1-6}$alkyl, or —CON(C$_{1-6}$alkyl)$_2$; or
  (m) —OCONHC$_{1-6}$alkyl or —OCONH$_2$;

R$_1$ is
(1) R'NH— wherein R' represents
  (A) H;
  (B)

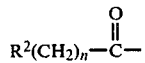

where R$^2$ represents
  (a) H;
  (b) C$_{1-3}$alkyl;

(c) $CF_3$;
(d) $-CH_2-O-C_{1-3}$alkyl;
(e) $-CH_2CN$;
(f) thienyl;
(g) phenyl or substituted phenyl as previously defined; n is an integer of 0 to 2;
(C) $R^2-X_1-(CH_2)_nCO-$ wherein $X_1$ is O or S; $R^2$ and n are as defined previously; or
(D)

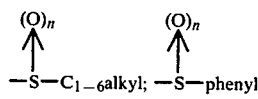

or substituted phenyl wherein substituted phenyl is as previously defined; and n is 0, 1 or 2;
(2) amino, $-NHC_{1-6}$alkyl, or $-N(C_{1-6}$alkyl$)_2$;
(3) nitro;
(4) azido;
(5) nitroso;
(6) isocyanato;
(7) isothiocyanato;
(8) hydroxyamino; or
(9) $-CONH_2$, $-CONHC_{1-6}$alkyl, or $-CON(-C_{1-6}$alkyl$)_2$;

B is
(1) $OB_1$ wherein $B_1$ is
(a) $C_{1-6}$alkyl;
(b) $C_{1-6}$alkenyl;
(c) $C_{1-6}$alkenoyl;
(d) $C_{1-6}$alkanoyl$C_{1-6}$alkyl;
(e) $C_{1-6}$alkanoyloxy$C_{1-6}$alkyl;
(f) $C_{1-6}$alkoxy$C_{1-6}$alkyl;
(g) $C_{1-6}$alkynyl;
(h) $-CH_2-$phenyl or $-CH_2$ substituted phenyl as defined above;
(i) phenyl or substituted phenyl as defined above;
(j) $C_{3-6}$cycloalkyl;
(k) halo$C_{1-6}$alkyl;
(2) $NB_2B_3$ wherein $B_2$ is $B_1$; and $B_3$ is $B_1$ or hydrogen; and Q is
(1) hydrogen;
(2) $C_{1-6}$alkyl;
(3) halo $C_{1-6}$alkyl;
(4) hydroxy$C_{1-6}$alkyl;
(5) [substituted or unsubstituted] methylene selected from a group consisting of
(a) $-CH_2$phenyl or $-CH_2$ sbustituted phenyl as defined above;
(b) $-CH_2-S$-phenyl or substituted phenyl as defined above;
(c) $-CH_2SO$-phenyl or substituted phenyl as defined above;
(d) $-CH_2-SO_2$-phenyl or substituted phenyl as defined above;
(6) $C_{1-6}$alkoxy$C_{1-6}$alkyl;
(7) [unsubstituted or substituted benzyl]$-CH_2$-phenyl or $-CH_2$-substituted phenyl as previously defined;
(8) phenyl-O$-C_{1-6}$alkyl or substituted phenyl-O$-C_{1-6}$alkyl wherein the substituted phenyl is as previously defined;
(9) phenyl-NH$-C_{1-6}$alkyl or substituted phenyl-NH$-C_{1-6}$alkyl wherein the substituted phenyl is as previously defined.

2. The composition of claim 1 wherein M is
(1) trifluoromethyl;
(2) chloro or fluoro;
(3) $-COOH$;
(4) $-CHO$; or
(5) $-CH_2A$ wherein A represents
(a) hydrogen;
(b) halo;
(c) hydroxy;
(d) $C_{1-6}$alkoxy;
(e) $-O$-phenyl or $-O-$substituted phenyl wherein the substituted phenyl is as previously defined;
(f) $-OCH_2$-phenyl or $-OCH_2$-substituted phenyl as previously defined;
(g) $-S-R_5$ wherein $R_5$ is $C_{1-6}$alkyl or phenyl;
(h) $-SCOR_5$ wherein $R_5$ is $C_{1-6}$alkyl or phenyl;
(i) $C_{1-6}$alkanoyloxy; or
(j) $-OCONH_2$ or $-OCONHC_{1-6}$alkyl;

$R_1$ is $R'NH-$ wherein $R'$ is
(1)

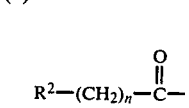

wherein $R^2$ represents:
(a) hydrogen;
(b) methyl or $CF_3$;
(c) thienyl;
(d) phenyl; or
(e) mono- and disubstituted phenyl and thienyl wherein the substituents are selected from the group consisting of chloro, fluoro, nitro, $C_{1-6}$alkyl, and $C_{1-6}$alkoxy; n is 0 or 1; or
(2)

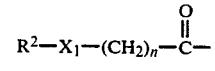

where $X_1$ is oxygen or sulfur; $R^2$ and n are as previously defined;
B is $OB_1$ of $NB_2B_3$ wherein $B_1$ and $B_2$ independently are as previously defined;
$B_3$ is hydrogen or $B_1$; and
Q is hydrogen.

3. The composition of claim 2 wherein M is
(1) trifluoromethyl;
(2) chloro or fluoro;
(3) $-COOH$; or
(4) $-CH_2A$ wherein A represents
(a) $C_{1-6}$alkanoyloxy;
(b) $C_{1-4}$alkoxy;
(c) halo;
(d) hydrogen;
(e) hydroxy;
(f) $-S-R_5$; or
(g)

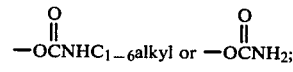

$R_1$ is
$R'NH-$ wherein $R'$ represents $$R^2-\overset{O}{\underset{\|}{C}}-$$

wherein $R^2$ is
(a) trifluoromethyl;
(b) methyl;
(c) methoxy;
(d) hydrogen;
(e) benzyl;
(f) phenyl;
(g) 2-thienylmethyl;
(h) phenylthiomethyl;
(i) phenoxymethyl;
(j) benzyloxy;
(k) $NCCH_2SCH_2$;

B is $OB_1$ or $NB_2B_3$ wherein
$B_1$ and $B_2$ independently represent
(1) benzyl;
(2) ethyl;
(3) t-butyl;
(4) $-CH_2CH_2CH=CH_2$; or $-CH_2CH=C(CH_3)_2$;
(5) $-CH_2CH_2CH_2COOt-Bu$;
(6) $C_{1-6}$alkanoyloxymethyl; or
(7) $C_{1-6}$alkanoylmethyl; and
$B_3$ is hydrogen or $B_1$; and
Q is hydrogen.

4. A method of treating inflammatory or degenerating conditions which comprises the administration to a mammalian species in need of such treatment an effective amount of a compound of structural formula:

(I)

wherein M is:
(1) trifluoromethyl;
(2) chloro or fluoro;
(3) $-COOH$;
(4) $-CHO$; or
(5) $-CH_2A$ wherein A represents
(a) hydrogen;
(b) halo;
(c) hydroxy;
(d) $C_{1-6}$alkoxy;
(e) $-O-$phenyl or $-O-$substituted phenyl wherein the phenyl is substituted with one or more functional groups selected from a group consisting of $C_{1-6}$alkyl, $C_{1-6}$alkoxy, $C_{1-6}$alkylthio, $C_{1-6}$alkanoyl, $C_{1-6}$alkanoyloxy; nitro, $C_{1-6}$alkylamino, amino, halo, $CF_3$, $CF_3S-$, $C_{1-6}$alkylsulfinyl and $C_{1-6}$alkylsulfonyl;
(f) $-OCH_2$phenyl or $-OCH_2$-substituted phenyl wherein the substituted phenyl is as previously defined;
(g)

$$\overset{(O)_n}{\underset{\uparrow}{-S-R_5}}$$

wherein $R_5$ is $C_{1-6}$alkyl, phenyl, substituted phenyl, $-CH_2$-phenyl or $-C_2$-substituted phenyl; n is an integer of 0-2;
(h) $-S-COR_5$;
(i) $C_{1-6}$alkanoyloxy;
(j) phenylcarbonyloxy;
(k) $-NH_2$, $-NHC_{1-6}$alkyl, or $-N(C_{1-6}$alkyl$)_2$;
(l) $-CONH_2$, $-CONHC_{1-6}$alkyl, or $-CON(C_{1-6}$alkyl$)_2$; or
(m) $-OCONHC_{1-6}$alkyl or $-OCONH_2$;

$R_1$ is
(1) R'NH— wherein R' represents
(A) H; (B)

$$R^2(CH_2)_n-\overset{O}{\underset{\|}{C}}-$$

where $R^2$ represents
(a) H;
(b) $C_{1-3}$alkyl;
(c) $CF_3$;
(d) $-CH_2-O-C_{1-3}$alkyl;
(e) $-CH_2CN$;
(f) thienyl;
(g) phenyl or substituted phenyl as previously defined; n is an integer of 0 to 2;
(C) $R^2-X_1-(CH_2)_nCO-$wherein $X_1$ is O or S; $R^2$ and n are as defined previously; or
(D)

$$\overset{(O)_n}{\underset{\uparrow}{-S-C_{1-6}\text{alkyl}}}; \quad \overset{(O)_n}{\underset{\uparrow}{-S-\text{phenyl}}}$$

or substituted phenyl wherein substituted phenyl is as previously defined; and n is 0, 1 or 2;
(2) amino, $-NHC_{1-6}$alkyl, or $-N(C_{1-6}$alkyl$)_2$;
(3) nitro;
(4) azido;
(5) nitroso;
(6) isocyanato;
(7) isothiocyanato;
(8) hyroxyamino; or
(9) $-CONH_2$, $-CONHC_{1-6}$alkyl, or $-CON(C_{1-6}$alkyl$)_2$;

B is
(1) $OB_1$ wherein $B_1$ is
(a) $C_{1-6}$alkyl;
(b) $C_{1-6}$alkenyl;
(c) $C_{1-6}$alkenoyl;
(d) $C_{1-6}$alkanoyl$C_{1-6}$alkyl;
(e) $C_{1-6}$alkanoyloxy$C_{1-6}$alkyl;
(f) $C_{1-6}$alkoxy$C_{1-6}$alkyl;
(g) $C_{1-6}$alkynyl;
(h) $-CH_2-$phenyl or $-CH_2$-substituted phenyl as defined above;
(i) phenyl or substituted phenyl as defined above;
(j) $C_{3-6}$cycloalkyl;
(k) halo$C_{1-6}$alkyl;
(2)$NB_2B_3$ wherein $B_2$ is $B_1$; and $B_3$ is $B_1$ or hydrogen; and Q is
(1) hydrogen;
(2) $C_{1-6}$alkyl;
(3) halo $C_{1-6}$alkyl;
(4) hydroxy $C_{1-6}$alkyl;

(5) methylene selected from a group consisting of
   (a) —CH₂phenyl or —CH₂ sbustituted phenyl as defined above;
   (b) —CH₂—S—phenyl or substituted phenyl as defined above;
   (c) —CH₂SO—phenyl or substituted phenyl as defined above;
   (d) —CH₂—SO₂-phenyl or substituted phenyl as defined above;
(6) C₁₋₆alkoxyC₁₋₆alkyl;
(7) —CH₂-phenyl or —CH₂-substituted phenyl as previously defined;
(8) phenyl-O—C₁₋₆alkyl or substituted phenyl—O—C₁₋₆alkyl wherein the substituted phenyl is as previously defined;
(9) phenyl—NH—C₁₋₆alkyl or substituted phenyl—NH—C₁₋₆alkyl wherein the substituted phenyl is as previously defined.

5. The method of claim 4 wherein: M is
(1) trifluoromethyl;
(2) chloro or fluoro;
(3) —COOH;
(4) —CHO; or
(5) —CH₂A wherein A represents
   (a) hydrogen;
   (b) halo;
   (c) hydroxy;
   (d) C₁₋₆alkoxy;
   (e) —O—phenyl or —O—substituted phenyl wherein the substituted phenyl is as previously defined;
   (f) —OCH₂-phenyl or —OCH₂-substituted phenyl as previously defined;
   (g) —S—R₅ wherein R₅ is C₁₋₆alkyl or phenyl;
   (h) —SCOR₅ wherein R₅ is C₁₋₆alkyl or phenyl;
   (i) C₁₋₆alkanoyloxy; or
   (j) —OCONH₂ or —OCONHC₁₋₆alkyl;
R₁ is R'NH— wherein R' is
(1)

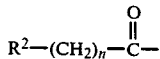

wherein R² represents:
(a) hydrogen;
(b) methyl or CF₃;
(c) thienyl;
(d) phenyl; or
(e) mono- and disubstituted phenyl and thienyl wherein the substitutents are selected from the group consisting of chloro, fluoro, nitro, C₁₋₆alkyl, and C₁₋₆alkoxy; n is 0 or 1; or
(2)

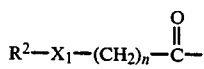

where X₁ is oxygen of sulfur; R² and n are as previously defined;
B is OB₁ of NB₂B₃ wherein B₁ and B₂ independently are as previously defined;
B₃ is hydrogen or B₁; and
Q is hydrogen.

6. The method of claim 4 wherein: M is
(1) trifluoromethyl;
(2) chloro or fluoro;
(3) —COOH; or
(4) —CH₂A wherein A represents (a) C₁₋₆alkanoyloxy;
(b) C₁₋₄alkoxy;
(c) halo;
(d) hydrogen;
(e) hydroxy;
(f) —S—R₅; or
(g)

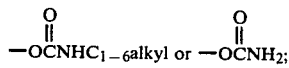

R₁ is
R'NH— wherein R' represents

wherein R² is
(a) trifluoromethyl;
(b) methyl;
(c) methoxy;
(d) hydrogen;
(e) benzyl;
(f) phenyl;
(g) 2-thienylmethyl;
(h) phenylthiomethyl;
(i) phenoxymethyl;
(j) benzyloxy;
(k) NCCH₂SCH₂;
B is OB₁ or NB₂B₃ wherein
B₁ and B₂ independently represent
(1) benzyl;
(2) ethyl;
(3) t-butyl;
(4) —CH₂CH₂CH=CH₂; or —CH₂CH=C(CH₃)₂;
(5) —CH₂CH₂CH₂COOt—Bu;
(6) C₁₋₆alkanoyloxymethyl; or
(7) C₁₋₆alkanoylmethyl; and
B₃ is hydrogen or B₁; and
Q is hydrogen.

7. A compound of the structural formula:

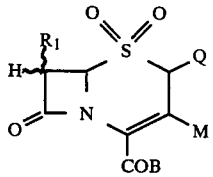

or a pharmaceutically acceptable salt thereof which is

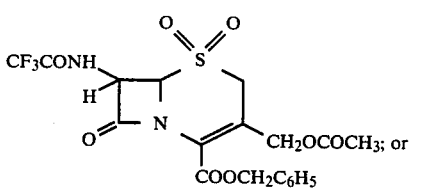

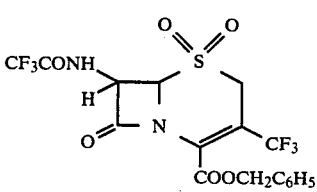

* * * * *